(12) United States Patent
Stoianovici et al.

(10) Patent No.: US 9,877,788 B2
(45) Date of Patent: Jan. 30, 2018

(54) MRI-SAFE ROBOT FOR TRANSRECTAL PROSTATE BIOPSY

(71) Applicant: THE JOHNS HOPKINS UNIVERSITY, Baltimore, MD (US)

(72) Inventors: Dan Stoianovici, Reisterstown, MD (US); Doru Petrisor, Lutherville Timonium, MD (US); Chunwoo Kim, Newton, MA (US); Peter Sebrechts, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 431 days.

(21) Appl. No.: 14/434,155

(22) PCT Filed: Oct. 8, 2013

(86) PCT No.: PCT/US2013/063808
§ 371 (c)(1),
(2) Date: Apr. 8, 2015

(87) PCT Pub. No.: WO2014/058833
PCT Pub. Date: Apr. 17, 2014

(65) Prior Publication Data
US 2015/0265354 A1    Sep. 24, 2015

Related U.S. Application Data

(60) Provisional application No. 61/710,909, filed on Oct. 8, 2012.

(51) Int. Cl.
*A61B 19/00* (2006.01)
*A61B 5/055* (2006.01)
(Continued)

(52) U.S. Cl.
CPC .......... *A61B 19/2203* (2013.01); *A61B 5/055* (2013.01); *A61B 5/4381* (2013.01);
(Continued)

(58) Field of Classification Search
CPC . A61B 10/0241; A61B 10/0275; A61B 10/04; A61B 19/2203; A61B 2010/0208;
(Continued)

(56) References Cited

U.S. PATENT DOCUMENTS

| 5,916,175 A | 6/1999 | Bauer |
| 2010/0041938 A1 | 2/2010 | Stoianovici et al. |

(Continued)

*Primary Examiner* — Michael Rozanski
(74) *Attorney, Agent, or Firm* — Johns Hopkins Technology Ventures

(57) ABSTRACT

An MRI safe robot for guiding transrectal prostate biopsy comprises a support arm, a robot body operatively connected to the support arm and a transrectal biopsy device operatively connected to the robot body. The transrectal biopsy device includes an endorectal extension and a biopsy needle device, the endorectal extension including an MRI coil for MRI imaging of the prostate. The robot body includes a first driver module for generating rotational motion of the endorectal extension and a second driver module for angulating the biopsy needle device toward a target area of the prostate for biopsy. The biopsy needle device is rotatable relative to the endorectal extension about a fixed axis and translatable through the endorectal extension. Each of the first and second driver modules include at least one pneumatic motor, wherein the MRI images are used by a physician to determine the target area for biopsy.

14 Claims, 18 Drawing Sheets

(51) Int. Cl.
- *A61B 10/04* (2006.01)
- *G01R 33/28* (2006.01)
- *G01R 33/48* (2006.01)
- *A61B 10/02* (2006.01)
- *A61B 5/00* (2006.01)
- *A61B 34/30* (2016.01)
- *A61B 90/11* (2016.01)
- *A61B 17/00* (2006.01)
- *A61B 90/00* (2016.01)

(52) U.S. Cl.
CPC .............. *A61B 5/742* (2013.01); *A61B 5/748* (2013.01); *A61B 10/0241* (2013.01); *A61B 10/0275* (2013.01); *A61B 10/04* (2013.01); *A61B 34/30* (2016.02); *A61B 90/11* (2016.02); *A61B 90/39* (2016.02); *G01R 33/287* (2013.01); *G01R 33/48* (2013.01); *A61B 2010/0208* (2013.01); *A61B 2010/045* (2013.01); *A61B 2017/00544* (2013.01); *A61B 2090/062* (2016.02); *A61B 2090/374* (2016.02); *A61B 2090/3954* (2016.02)

(58) Field of Classification Search
CPC .... A61B 2010/045; A61B 2017/00544; A61B 2090/062; A61B 2090/374; A61B 2090/3954; A61B 34/30; A61B 5/055; A61B 5/4381; A61B 5/742; A61B 5/748; A61B 90/11; A61B 90/39; G01R 33/287; G01R 33/48

See application file for complete search history.

(56) References Cited

U.S. PATENT DOCUMENTS

| | | |
|---|---|---|
| 2010/0049086 A1 | 2/2010 | Hibner et al. |
| 2010/0160823 A1 | 6/2010 | Parihar et al. |
| 2011/0178390 A1 | 7/2011 | Li |

MRI-SAFE ROBOT FOR TRANSRECTAL PROSTATE BIOPSY

CROSS-REFERENCE TO RELATED APPLICATIONS

This application is a 35 U.S.C. §371 U.S. national entry of International Application PCT/US2013/063808 having an international filing date of Oct. 8, 2013, which claims the benefit of U.S. Provisional Application No. 61/710,909, filed Oct. 8, 2012, the content of each of the aforementioned applications is herein incorporated by reference in their entirety.

GOVERNMENT SUPPORT

This invention was made with government support under W81XWH-08-1-0221 awarded by the Department of Defense. The government has certain rights in the invention.

FIELD OF THE INVENTION

The present invention relates to medical devices. More particularly, the present invention is related to a MRI-safe robot for transrectal prostate biopsy.

BACKGROUND OF THE INVENTION

In 2012, an estimated 241,740 new prostate cancer (PCa) cases will be diagnosed in the US alone. A large number of these represent indolent tumors unlikely to limit the lifespan of the patient. A recent study has shown that it is necessary to treat 48 men to prevent one death from PCa, suggesting that significant overtreatment exists. Still, many PCa are aggressive, causing an estimated 28,170 mortalities this year. Therefore, a more comprehensive diagnostic approach is needed to differentiate indolent and harmless tumors from aggressive and lethal PCa in individual patients.

The most common way of diagnosing PCa is the transrectal ultrasound (TRUS) guided prostate biopsy. But, standard gray-scale ultrasound is unreliable in differentiating PCa from normal tissues. The biopsy procedures are cancer "blind", aiming to sample the gland systematically in search of possible tumors. Because PCa is a heterogeneous multi-focal disease, with untargeted biopsy both overdiagnosis of clinically insignificant cancer and underdiagnosis of potentially lethal cancer exist in the population at risk.

Accurate PCa targeted biopsy has the potential to 1) reduce the randomness that yields clinically insignificant cancer and leads to overdiagnosis, and 2) increase the likelihood of sampling the most advanced CSR reducing the underdiagnosis of potentially lethal cancer.

Novel genomic, proteomic, and image biomarkers are currently investigated to more reliably diagnose and assess the aggressiveness of PCa. In addition to other tests and biomarkers of higher specificity, a critical component needed to address this problem is a more reliable way to biopsy the gland.

As mentioned above, the most common way of diagnosing PCa is the transrectal ultrasound (TRUS) guided prostate biopsy. But, standard gray-scale ultrasound provides minimal PCa specific information being unreliable in differentiating PCa from normal gland tissues. The biopsy procedures are cancer "blind", relying instead on non-targeted template biopsy schemata that aim to sample the gland systematically in search of possible tumors. Yet biopsies do not sample the entire gland because the number of cores is limited (typically 12). For an exhaustive, saturation biopsy the number of biopsy cores is very high making them impractical for most patients and the common transrectal biopsy path.

Because PCa is a heterogeneous multi-focal disease, untargeted biopsies often yield to the detection of small, clinically insignificant tumors and/or miss significant cancers (i.e. >0.5 mL). Moreover, due to limited technology, the common manually-operated TRUS-guided biopsy is difficult and quality control is subjective. Studies have shown the biopsy schema is difficult to define and follow, resulting in biopsy samples that are clustered and miss regions of the gland. While these errors have less impact on the detection of small tumors, the detection rate of clinically significant lesions is worsened. Studies have shown that the histologic grade from TRUS biopsy samples is often underestimated compared to prostatectomy specimens. Systematic TRUS biopsies have typically low sensitivity and low negative predictive value. With untargeted biopsy, both overdiagnosis of clinically insignificant cancer and underdiagnosis of potentially lethal cancer exist in the population at risk.

A noticeable solution to sample significant cancer is cancer-image guided targeting. Accurate biopsy targeting to cancer suspicious regions (CSR) of image abnormality has the potential to 1) reduce the randomness that yields clinically insignificant cancer and leads to overdiagnosis, and 2) increase the likelihood of sampling the most advanced CSR, thereby reducing the underdiagnosis of potentially lethal cancer.

CSR targeting for biopsy relies heavily on the ability of imaging to depict CSRs. Among other imaging modalities, magnetic resonance imaging (MRI) provides the highest spatial and contrast resolution for prostate anatomy. Functional MRI imaging techniques (MR spectroscopy (MRSI), diffusion-weighted (DWI), and dynamic contrast-enhanced (DCE)) have shown substantial potential to complement T2-weighted MRI in improving PCa localization. These imaging approaches and PCa image biomarkers still require further validation and have recognized limitations, including the potential for false positive and false negative results. Although not perfect and still under development, using image findings to target regions with the highest probability of advanced cancer has great potential. Even though no current imaging method can absolutely differentiate benign from malignant lesions, imaging could point to abnormalities that should be biopsied.

One of the simplest methods of biopsy targeting is MRI-TRUS image fusion. With this method, MRI is acquired ahead of time, the biopsy is guided as usual based on the TRUS, but the MRI is fused (registered) to the interventional ultrasound for CSR targeting. Associated biopsy technologies include probe tracking devices such as magnetic sensors (Logiq-E9 system, GE Healthcare, Waukesha, Wis.) and positioning arms (Artemis, Eigen, Grass Valley, Calif.). Several clinical studies reported increased detection rates of significant cancer by CSR targeting. Technically, the accuracy of these systems relies on challenging cross-modality image-to-image registration and deformable registration methods. Images had been previously acquired using MRI, a different imaging modality than TRUS, with the patient in a different position and endorectal MRI coil compressing the gland. At biopsy, the TRUS probe also deforms the gland but differently and dynamically. These differences contribute to targeting errors that are difficult to quantify. Also, the means of verifying the registration are very limited, especially after the initial alignment. MRI-TRUS fused biopsy methods offer logistic advantages, maintain the traditional use of TRUS for biopsy, and are likely superior to traditional systematic methods. Yet their navigation requires further validation and it remains to be tested if these are sufficiently accurate to make a clear clinical difference.

A more involved but promising method of CSR targeting is to directly use the MRI for guiding the intervention, interventional MRI-guided biopsy. The main claim of this approach is a potentially superior targeting accuracy, by eliminating several error components such as pre-acquired to interventional image differences, image differences between the imaging modalities, and image fusion errors.

A few groups investigated the use of manually operated needle-guide devices in the MRI scanner. Several high-dose brachytherapy cases using a needle-guide template registered to the MRI have been performed at the NIH clinical center (Bethesda, Md.). Transperineal biopsy and brachytherapy procedures were performed at the Brigham and Women's Hospital (Boston, Mass.) in a 0.5T open MRI scanner. They also reported a transperineal prostate biopsy in a patient with recurrent PC after brachytherapy and showed that MRI guidance was useful for targeting. In Germany, two studies reported MRI guided biopsies in patients with elevated PSA levels and without previous TRUS guided biopsies and for repeat biopsies. A plastic transrectal biopsy device that allows manual angulation of a needle guide was developed by Invivo (Schwerin, Germany). But, its operation is time consuming and it can't be used with an endorectal coil, which limits the quality of prostrate imaging. A more advanced biopsy device was used at the NIH in a closed-bore 1.5T scanner. This incorporated an imaging coil, special position tracking coils, and a needle guide. They showed improved cancer detection in MRI-guided biopsies when the MRI-guided biopsy was not immediately following the TRUS-guided biopsy. But commonly, the manual devices were difficult to operate due to the limited access within the scanner and numerous table moves were required to access the patient.

A noticeable solution to guide the needle remotely in the MRI scanner is to employ robotic assistance. However, making a robot that can operate safely and accurately in the MRI scanner without being influenced by and without interfering with the functionality of the imager has been a very challenging engineering task.

Why is it Challenging to Make MRI Robots?

MRI scanners use magnetic fields of very high density (3 Tesla becoming common), with pulsed magnetic and radio frequency fields. Within the imager, ferromagnetic materials are exposed to very high magnetic interaction forces and heating may occur in conductive materials by electromagnetic induction. The use of electricity may cause interference leading to signal to noise attenuation, signal distortions, and image artifacts. As such, most of the components commonly used in robotics may not be used in close proximity of the MRI. For example, the ubiquitous electromagnetic motor is clearly MRI unsafe because it functions based on magnetism.

MRI-Safe, MRI-Conditional, and MRI-Unsafe ASTM Classification:

The American Society for Testing and Materials (ASTM) has set a series of standards to test (ASTM F2213, F2182, F2119) and classify (ASTM F2503) devices for the MRI environment. In short, devices are:

MRI-Safe ▪ Is an item that poses no known hazards in all MR environments.

MRI-Conditional ▲ Is an item that has been demonstrated to pose no known hazards in a specified MR environment with specified conditions of use. Field conditions that define the specified MR environment include field strength, spatial gradient, dB/dt (time rate of change of the magnetic field), radio frequency (RF) fields, and specific absorption rate (SAR).

MRI-Unsafe ⊛ Is an item that is known to pose hazards in all MR environments.

What are Ideal "MRI Safe" Materials and Energy Types?

Several non-ferrous metals such as titanium and nitinol have been found to be MRI-Conditional for small size parts and are used in commercial MRI passive devices (Biopsy needles for example). However, for noninterference with electro-magnetism the ideal materials should be not only nonmagnetic but also dielectric, such as plastic, rubber, and glass. Interestingly, carbon fiber is not MRI-Safe because it is a good electrical conductor. From the energetic point of view, the use of electricity will likely exclude the MRI-Safe option, because currents generate electromagnetic waves and require wires that are not dielectric. Electric devices could be MRI-Conditional at best. Pneumatics and light on the other hand are ideal MRI-Safe energy choices, because they are completely decoupled from electromagnetism.

Most previous attempts to make MRI-guided robots used piezoelectric actuators (motors, also called ultrasonic). These are magnetism free but use metallic components and electricity which typically affect the quality of MR images. Even without power, it was shown that the wiring may debase the signal-to-noise-ratio by as much as 50%. Electric screening and filtering solutions have been employed to cope with these problems and incremental gain was progressively achieved. Two representative examples of piezo-actuated robots are the Brigham and Women's Hospital (Boston, Mass.) system for open-MRI which had to be located distal above the scanner, and the recent NeuroArm from the University of Calgary (Canada) which normally operates in the MRI room but not in the scanner. Moreover, piezoelectric robots may only be MRI-Conditional but not MRI-Safe. Scientifically, since PCa imaging is still under development, it is preferable that no image artifact compromise should be made to use the biopsy device in the scanner and that MRI sequences should not be limited to certain types that provide less problems with the device.

Hydraulic actuation may be MRI-Safe if properly constructed of nonmetallic materials. However, fluid leakage is difficult to control, especially when nonmetallic components are used. For medical applications this raises contamination and sterility concerns. As such, hydraulic MRI robot approaches maintained the use of metallic components.

Pneumatic actuation is a fundamentally flawless MRI-safe option. But, the major limitation of classic pneumatic actuators is their notoriously difficult motion control. Pneumatic servo control is a very delicate problem, because the compressibility of the air and the stiction of the piston make the system highly nonlinear and hardly manageable. Pneumatic servo control in the MRI is even more intricate because long hoses are needed to connect them to pneumatic valves, which are typically located distal from the scanner. Moreover, pneumatic cylinders have another major problem for medical applications: they are direct drive actuators. If they malfunction, direct drives may swiftly spring off, fully and quickly unwinding and potentially hurting the patient or personnel. Medical applications require small, slow, precise, and safe actuation. A direct-drive actuator that is also hardly controllable represents a safety concern. As such, researchers devised a good solution implementing breaks for safety. But unfortunately, due to all the additional complexity, the robots still included metallic components and were shown to debase the signal to noise ratio of the MRI. The former Innomotion company (Germany) devised a very ingenious purpose built pneumatic cylinder to help its control. This increased the sliding friction relative to the stiction in order to reduce the unfavorable influence of the later in servo-control. Unfortunately, this cylinder remained highly sensitive to disturbances such as small temperature changes.

A pneumatic turbine based motor was recently reported from the Nijmegen Medical Centre in the Netherlands and the device is entirely built of nonmetallic components. This represents a very promising MRI-safe engineering solution. The device applies to direct MRI-guided endorectal prostate biopsy and is the first actuated device for the application to be tested clinically. But apparently the actuators of device are not encoded yet, or the feedback is not being used for control so that the device is not a robot but remotely controlled by the physician observing the MRI. This is an especially difficult task because the MRI has relatively long acquisition times.

Hitherto, very few interventional MRI-guided prostate biopsy devices have been tested clinically in very few patients. Yet, these have shown the feasibility of interventional MRI and CRS biopsy targeting. The rational of biopsy targeting to improve selectively the detection of significant PCa appears to be sound, but further device refinements and clinical validations are needed to evaluate its clinical role. Accordingly, there is a need in the art for biopsy targeting to improve the detection of PCa.

SUMMARY

According to a first aspect of the present invention, an MRI safe robot for guiding transrectal prostate biopsy comprises a support arm, a robot body operatively connected to the support arm, a transrectal biopsy device operatively connected to the robot body, the transrectal biopsy device including an endorectal extension and a biopsy needle device, the endorectal extension including an MRI coil for MRI imaging of the prostate, and the robot body including a first driver module for generating rotational motion of the endorectal extension and a second driver module for angulating the biopsy needle device toward a target area of the prostate for biopsy, the biopsy needle device being rotatable relative to the endorectal extension about a fixed axis and translatable through the endorectal extension, each the first and second driver modules including at least one pneumatic motor, wherein the MRI images are used by a physician to determine the target area for biopsy.

According to a second aspect of the present invention, a robot-assisted method for biopsy of a prostate comprises providing a robot including a transrectal biopsy device having an endorectal extension powered by a first pneumatic motor and a biopsy needle device powered by a second pneumatic motor, the endorectal extension including an MRI coil for MRI imaging of the prostate, imaging a target area of interest by MRI imaging, displaying the MRI images, selecting a target area of interest based upon the MRI images, and directing the robot to automatically orient the transrectal biopsy device towards the target area selected by rotating the endorectal extension and angulating the biopsy needle device.

According to a third aspect of the present invention, a remote robotic device for presetting a depth of needle insertion of a biopsy device comprises a biopsy needle device including a handle connected to a biopsy needle, the biopsy needle including a threaded portion for receiving a spacer nut, and a non-threaded portion for taking a biopsy, wherein needle depth is adjusted by controlled rotation of the spacer nut by a nut driver.

According to a fourth aspect of the present invention, a method for targeting a gland of interest for biopsy comprises providing a robot for biopsy of the gland of interest with three degrees of freedom, said robot including a biopsy device, the biopsy device including an extension member operatively connected to a needle guide, rotating the extension member about a longitudinal axis of the extension member in a first degree of freedom, rotating the needle guide relative to the extension member about a fixed axis in a second degree of freedom, and presetting a depth of needle insertion by translating the biopsy needle in a third degree of freedom, the third degree of freedom being remote.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIG. 14 (*b*) is a graphical representation of the active (A) coefficients as a function of the axial image slice from the phantom toward the robot according to the features of the present invention.

FIG. 17(*b*) illustrates an example of the image navigation screen showing the superimposed registration markers, the prostate and the inserted needle model of an MRI-guided biopsy animal experiment according to the features of the present invention.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention pertains to an MRI-Safe motor technology. As shown above, the existing types of motors are unsuitable for the MRI environment, because no motor can satisfy the reliability, precision, and safety required for a medical robot to function in the MRI without interfering with its functionality. In short, available options may be either MRI-unsafe, or imprecise and unsafe, or cause image distortions.

The present invention includes, in part, a pneumatic step motor configured for use with an MRI machine. Electric step motors are ubiquitous in digital devices such as printers. But the PneuStep was the first motor to step with air pressure. The advantage of stepping compared to pneumatic servo-control, is that motion is inherently precise because the size of the steps is independent of the driving air pressure. As shown in the Background section, pneumatic servo-control is notoriously difficult and susceptible to disturbances. Moreover, the PneuStep is entirely constructed of MRI-Safe materials, which are nonmagnetic and dielectric such as plastics and rubbers. Its sensors (position encoders) are built with fiber optics, so that the motor is electricity free.

Figure 1:
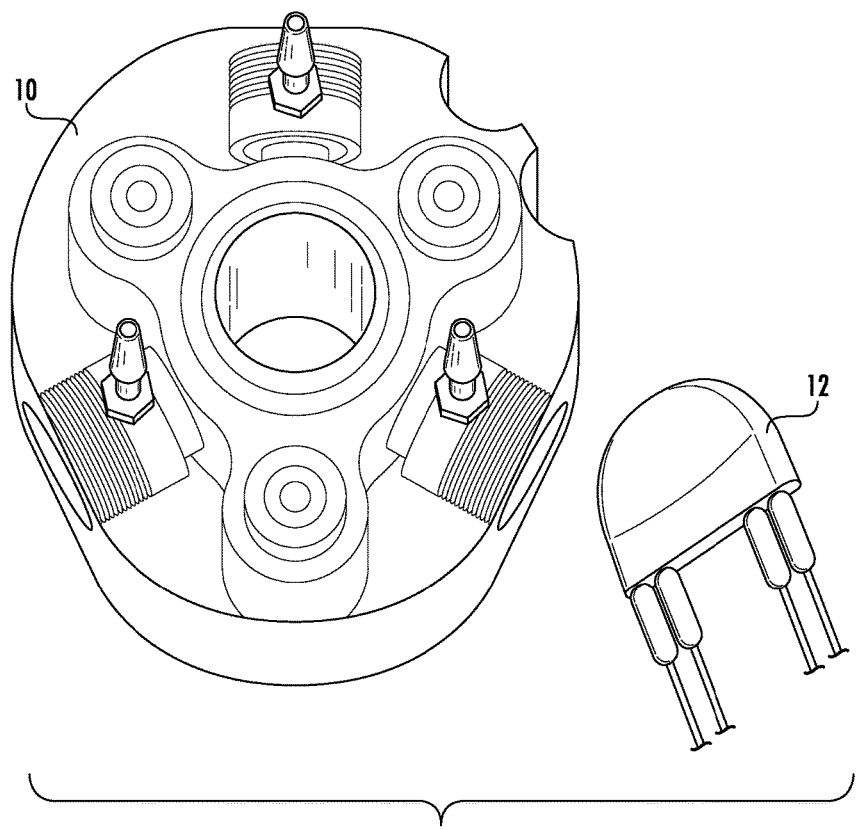
FIG. 1 illustrates a perspective view of the PneuStep Motor used in the MRI biopsy robotic device according to the features of the present invention.

For the MRI robot the PneuStep has been revised with a more compact size, improved optical encoders, and control hardware. A photograph of the new motor 10 is presented in FIG. 1, showing its fiber optic sensor 12 detached. Comprehensive tests have shown that the PneuStep operates precisely and without interfering with the MRI, even if located at the image isocenter of virtually any magnetic field imager. The PneuStep satisfies the combined MRI-safe, image non-interference, precision, safety and reliability required for MRI-guided devices. The PneuStep makes the technology base of the biopsy robot device.

Another component of the present invention is a novel robotic-assistance device for endorectal prostate biopsy. The device assists the physician by automatically orienting a needle-guide on target and setting the depth of needle insertion under MRI guidance. The target is selected by the physician in the MRI. Needle insertion and biopsy are performed manually, as usual, but both are guided by the device. A perspective view of the robot is presented in FIG. 2.

Figure 2:
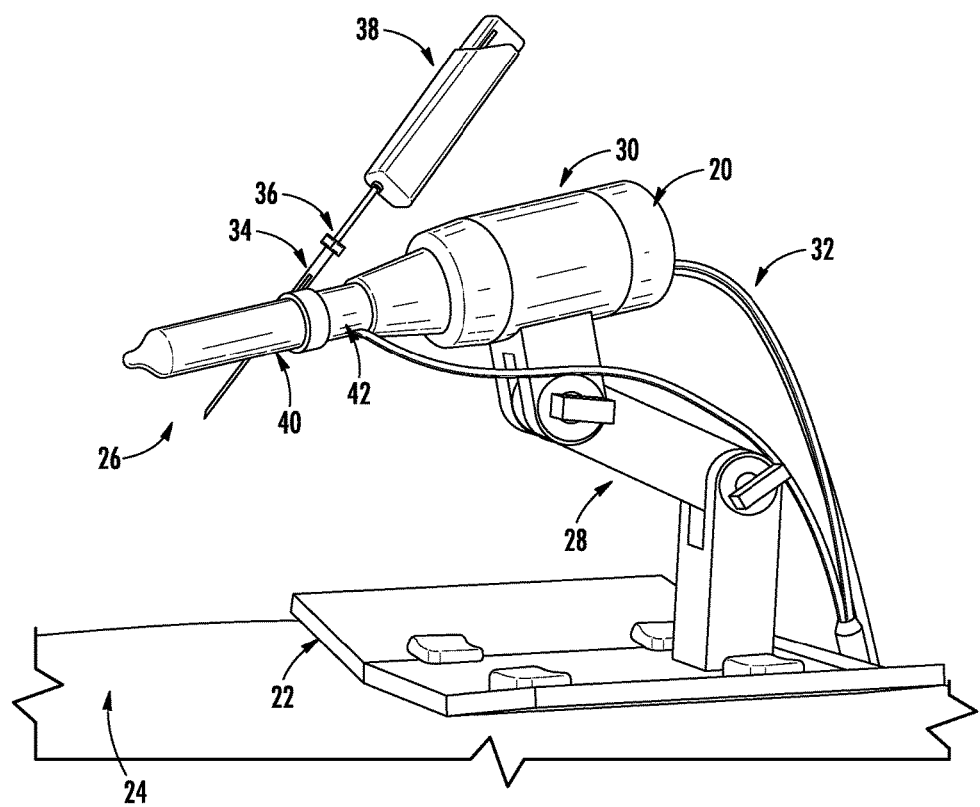
FIG. 2 illustrates a perspective view of an exemplary robotic assistant device according to the features of the present invention.

As illustrated in FIG. 2, the robot 20 attaches with a base plate 22 to the MRI couch 24. The robot 20 is attached to the couch 24, after placing the patient on the couch 24 in the prone position. An endorectal extension 26 is then placed manually, like a TRUS probe or endorectal MRI coil. A support arm 28 is locked in place to maintain this position throughout the procedure. Robotic motion is generated by pneumatic motors located within a body 30 of the robot 20. These are controlled with air and light through a bundle of hoses 32 that connects the robot to an interface and controller, described later in this section. The robot 20 also includes a needle guide 34 and a needle spacer 36 configured to couple with a biopsy needle 38.

The endorectal extension, preferably, includes an MRI coil 40. This is an integrated component of the endorectal-pelvic phased-array coils required to provide the highest spatial and contrast image resolution of the prostate. The endorectal extension also, preferably, includes a set of registration markers 42 for image-to-robot registration. The needle-guide 34 passes through the endorectal extension 26 at an angle that is automatically adjusted by the robot 20. The needle-spacer 36 is attached to the biopsy needle 38 so that the length of the needle can be adjusted based on the images. The length of the needle-spacer 36 is adjusted automatically, as shown later in this section.

Figure 3:
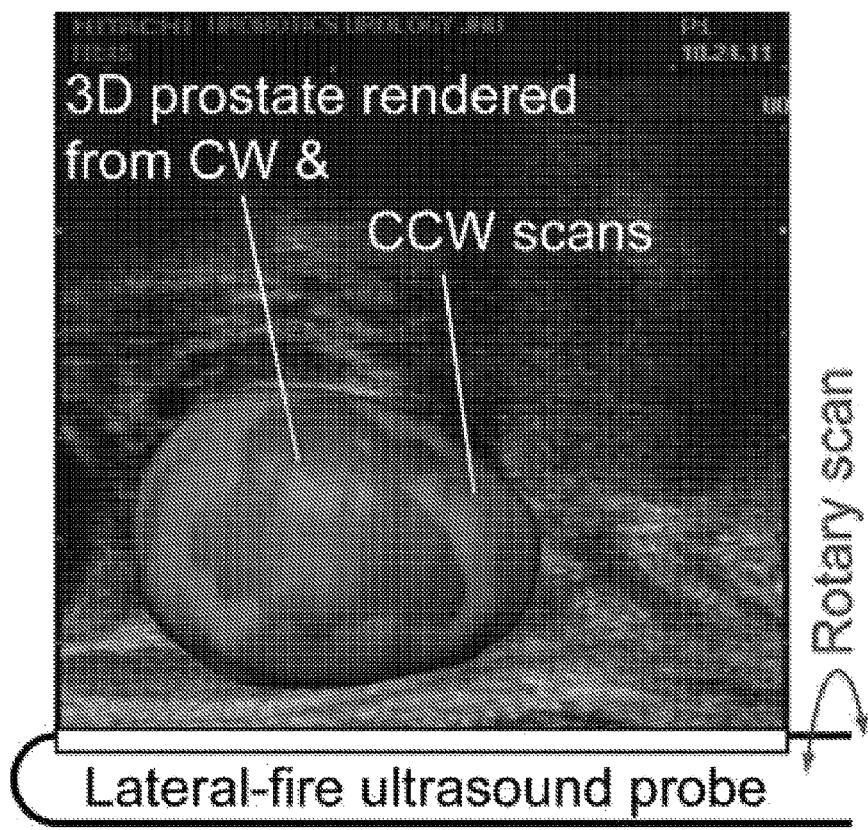
FIG. 3 illustrates an image of a lateral-fire parasagittal transrectal ultrasound of a patient according to the features of the present invention.

FIG. 3 shows a lateral-fire parasagittal TRUS of a patient. Purely rotary scans acquired in CW and CCW directions. Their segmentations show that the prostate was not deflected between the CW and CCW moves.

Robot Kinematics: The architecture and motion of the robot were optimized for the accuracy of prostate biopsy. For accurate image-guided biopsy, it is essential that at the time when the biopsy is targeted the prostate has not geometrically changed from its initially imaged state, based on which the biopsy target was selected. This implies that the motion of the device required to align the needle-guide on target should not move or deform (displace+deform=deflect) the gland. Preventing deflections circumvents the difficult task of correcting the trajectory to account for the deflections.

It is clinically verifiable that the prostate is not deflected if the endorectal extension is held in place and only rotated about its axis, with a rotary scan. FIG. 3 shows two manually segmented and 3D rendered prostate shapes from TRUS scanning the prostate with clockwise (CW) respectively counterclockwise (CCW) pure rotary scans. Differences between the two are very small, showing that rotation of an endorectal shaft does not deflect the prostate, provided that proper lubrication is provided, as usual.

Figure 4A:
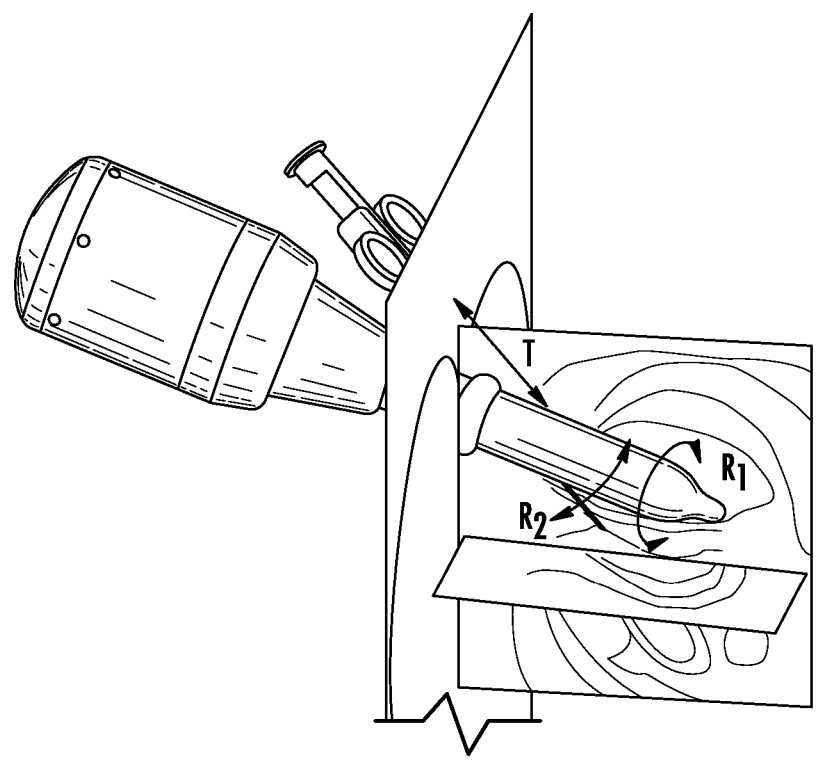
FIG. 4(a) illustrates a robot in CAD with MRI images of the prostate according to the features of the present invention.
Figure 4B:
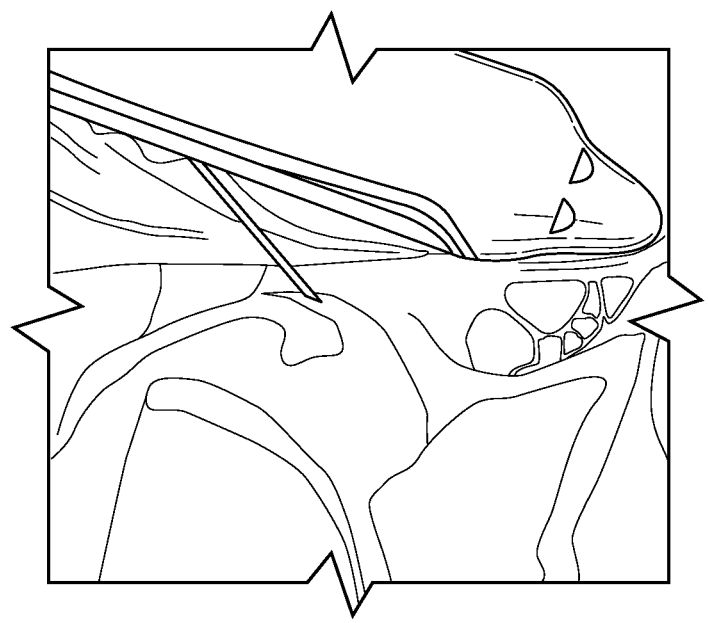
FIG. 4(b) illustrates the needle density plot in the central coronal slice according to the features of the present invention.

Based on the design requirements of minimizing prostate deflection, robot kinematics for the present invention are formulated with low DoF and purely rotary motion of the endorectal extension. Biopsy targeting was simulated in a combined Computer Aided Design (CAD)-MRI environment. For this, MRI images were registered to the robot space simulated in Creo (former Pro/Engineer, Parametric Technology Corporation, Needham, Mass.), as shown in FIGS. 4 (a) and (b). The robot was designed using mechanism components to simulate its motion. The simulation has shown that only 3-DoF are necessary and sufficient to target any gland location, where R1 is a rotation of the endorectal extension about its axis relative to the fixed robot body, R2 is a rotation of the needle-guide relative to the endorectal extension about a fixed axis, and T is a translation for inserting the needle through the needle-guide.

Figure 5:
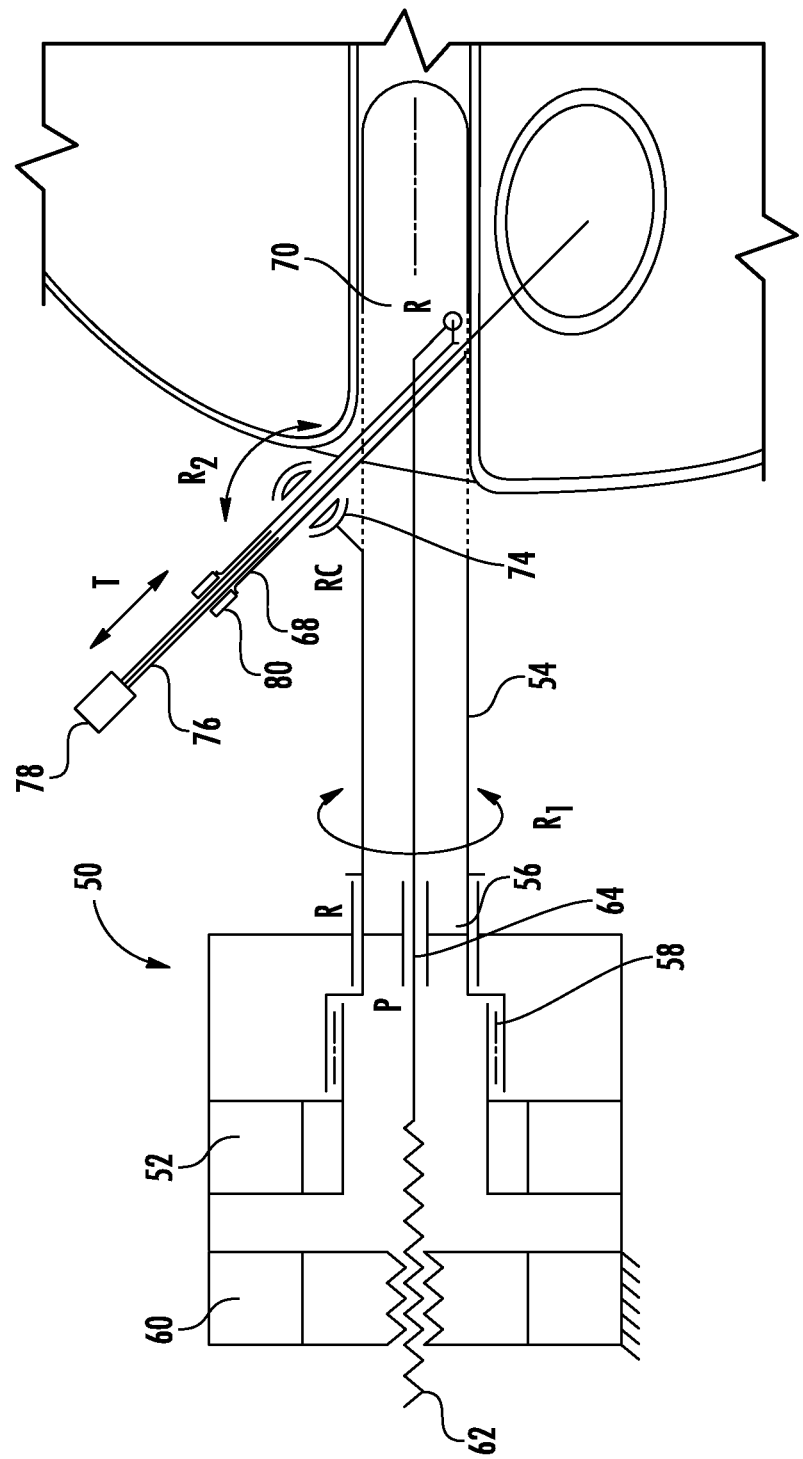
FIG. 5 illustrates a kinematic diagram of the robot with pelvic structures according to the features of the present invention.

The kinematic diagram of a robot 50 according to the present invention is presented in FIG. 5. A first motor 52 (Motor R1) adjusts the angle of the endorectal extension 54 (R1) supported by a revolute joint 56 (R) through a harmonic transmission 58. The second motor 60 (Motor R2) engages a screw transmission 62 supported by a prismatic joint 64 (P) and slides a bottom of the needle-guide 68 through a revolute joint 70 (R). A top of the needle-guide 68 slides through a revolute-cylindrical joint 74 (RC, zero link length) that is based on the endorectal extension 54. The needle-spacer 76 is attached to the needle 78 and a nut 80 is threaded to it. The position of the nut 80 over the spacer 76 is adjusted automatically by another component of the device. This remote DoF reduces the size and complexity of the robot 50. The needle 78 is inserted fully through the needle-guide 68 (T), until the nut 80 stops at the top of the needle-guide 68.

This kinematic architecture has been chosen based on several clinical considerations. The endorectal extension presents a cylindrical shape. Because the needle-guide passes through the endorectal extension and does not protrude at the bottom, rotations of the extension (R1) are unlikely to deflect the gland. The precision of targeting increases if the end of the needle-guide is as close as possible to the prostate. The revolute joint (R) at the bottom of the needle-guide keeps the guide as close as possible independent of its angulation. The location of the needle-guide angulation pivot at the top of the extension and as close as possible to the anus is an optimal solution to avoid the anal sphincter on the needle path. The architecture described above is unique.

Figure 6:
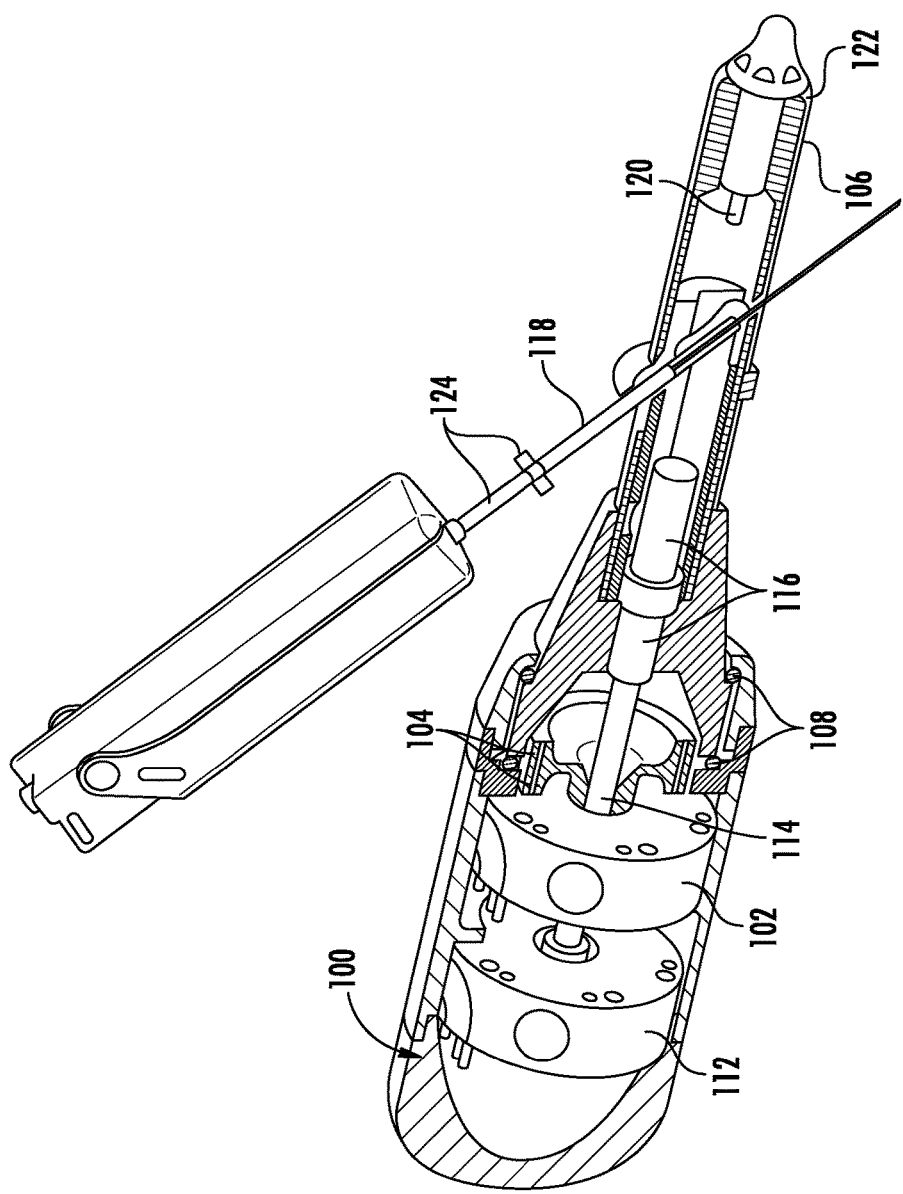
FIG. 6 illustrates a perspective view of the robot, with portions at the cross section removed according to the features of the present invention.

The robot was designed using the Creo CAD package including mechanism structures for kinematic simulation and analysis, and Geometric Element Analysis (GEA) for the structural analyses. A central cross-section of the robot design is shown in FIG. 6. The robot 100 uses a special type of motor, the PneuStep (pneumatic step motor), that we developed for the MRI. The PneuStep motor has a hollow output shaft, making it convenient to juxtapose the motors and passing the output through the other, as shown. The output of the R1 motor 102 engages a wave generator of a harmonic transmission 104. The output of the harmonic transmission 104 drives a part at the base of the endorectal extension 106. This is supported by two ball bearings 108 built within the parts. The second motor R2 112 drives a shaft 114 that passes through the first motor 102 and engages a screw transmission 116 actuating the angulation of the needle-guide 118. The endorectal extension 106 is assembled and removed by threading it into the body. One of the registration markers 120, part of the MRI coil 122, and the needle spacer 124 are also visible in FIG. 6.

Figures 7A, 7B, 7C:
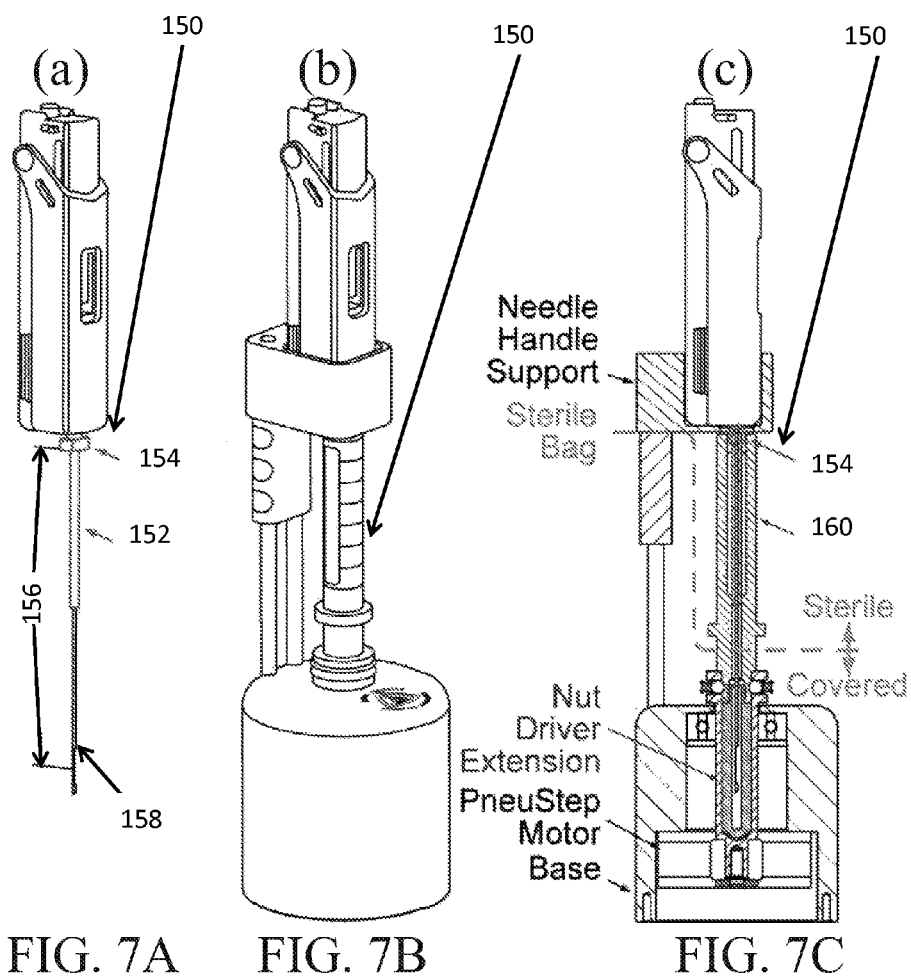
FIGS. 7 (a)-(c) illustrate perspective views of an exemplary needle depth driver according to the features of the present invention.

The design of the remote DoF for presetting the depth of needle insertion, the needle-spacer driver, is presented in FIG. 7(a)-(c). The spacer assembly 150 includes a threaded spacer shaft 152 and a spacer-nut 154. The device adjusts the needle depth 156 by controlled rotation of the spacer-nut 154. The needle 158 with the attached spacer-assembly 150 is placed in the device so that the handle rests within a support. Within the device the spacer-nut 154 intermeshes within a slot made in a nut driver 160. The nut driver 160 is connected to the output of a third PneuStep motor for controlled motion.

Figure 8:
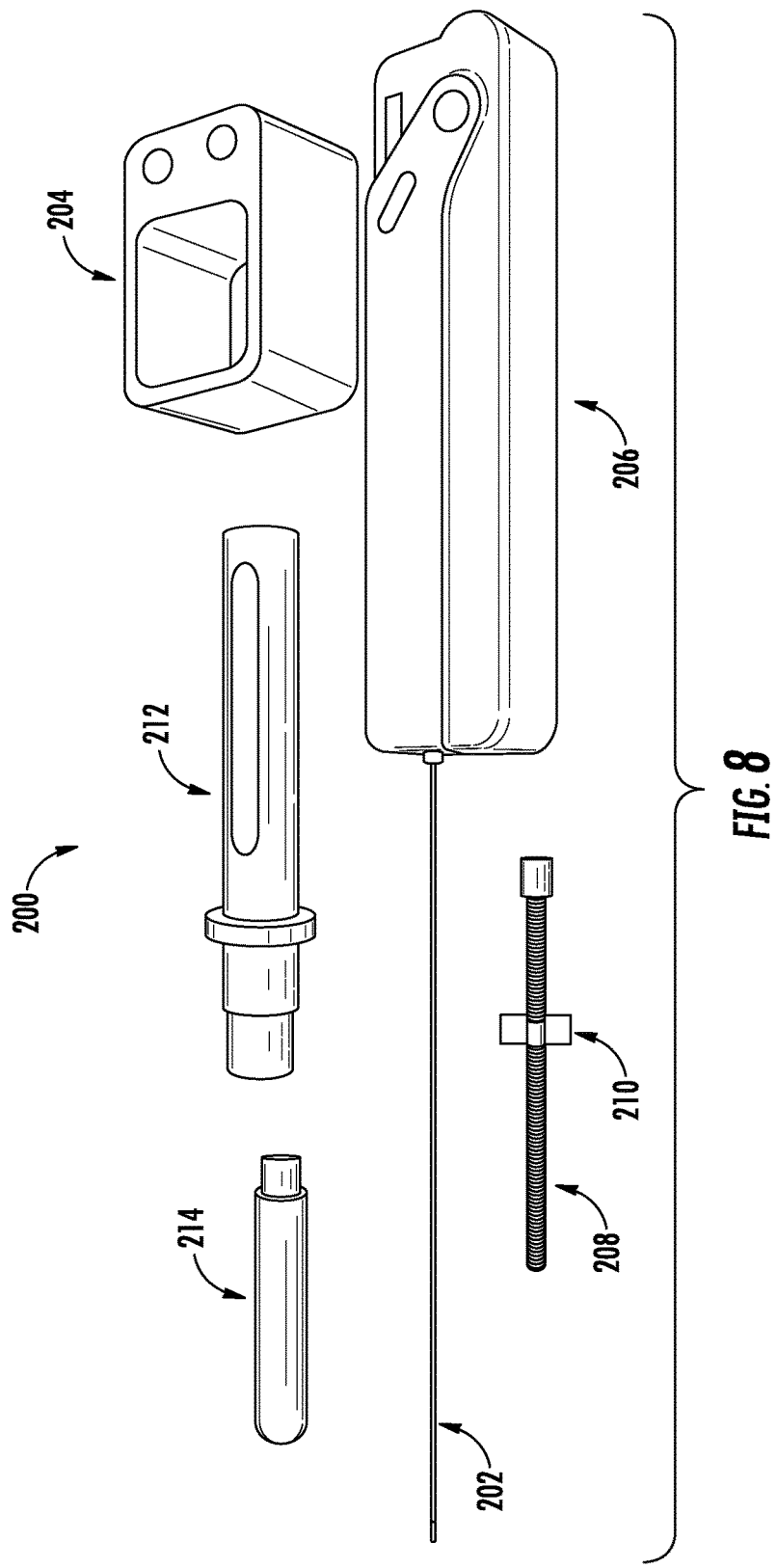
FIG. 8 illustrates a perspective view of the components of the needle-spacer driver that need to be sterilized according to the features of the present invention.

The robot and needle-spacer driver have been built with three identical PneuStep motors of Φ70×25 mm size and 6*15=90 steps/turn (FIG. 8). With the screw and harmonic transmissions the step resolutions are 0.082°/step, 28 µm/step, and 7 µm/step for the R1 axis, the linear drive of the R2 axis, and the needle-depth preset (T) respectively. All parts have been built of MRI-Safe materials such as plastics, rubbers, glass, and ceramics.

All parts that come in contact with the sterile needle must be sterile. Since in this version the needle-guide is not directly detachable, the endorectal extension must be sterilized. Thereafter, the endorectal extension is also covered with a condom, as usual, and the robot body is covered with a sterile bag (Universal Medical Inc., Foxboro, Mass., EZ-28).

The nut driver 160 is also covered with a sterile bag (sterile bag line in FIG. 7(c)) and the components that come or may come in direct contact with the needle are sterilized, as shown in FIGS. 7(a)-(c). These components can be easily assembled to the driver.

FIG. 8 illustrates an exemplary embodiment of a biopsy needle 200, according to an embodiment of the present invention. The biopsy needle assembly 200 includes a biopsy needle 202 and a support device 204, for supporting a handle 206, of the needle 202. A spacer shaft 208 and nut 210 are disposed on the shaft of the needle 202. The assembly 200 can also include a nut driver 212 and a nut driver extension 214. The assembly 200 is configured to be used with the robot of the present invention described herein.

Figure 9:
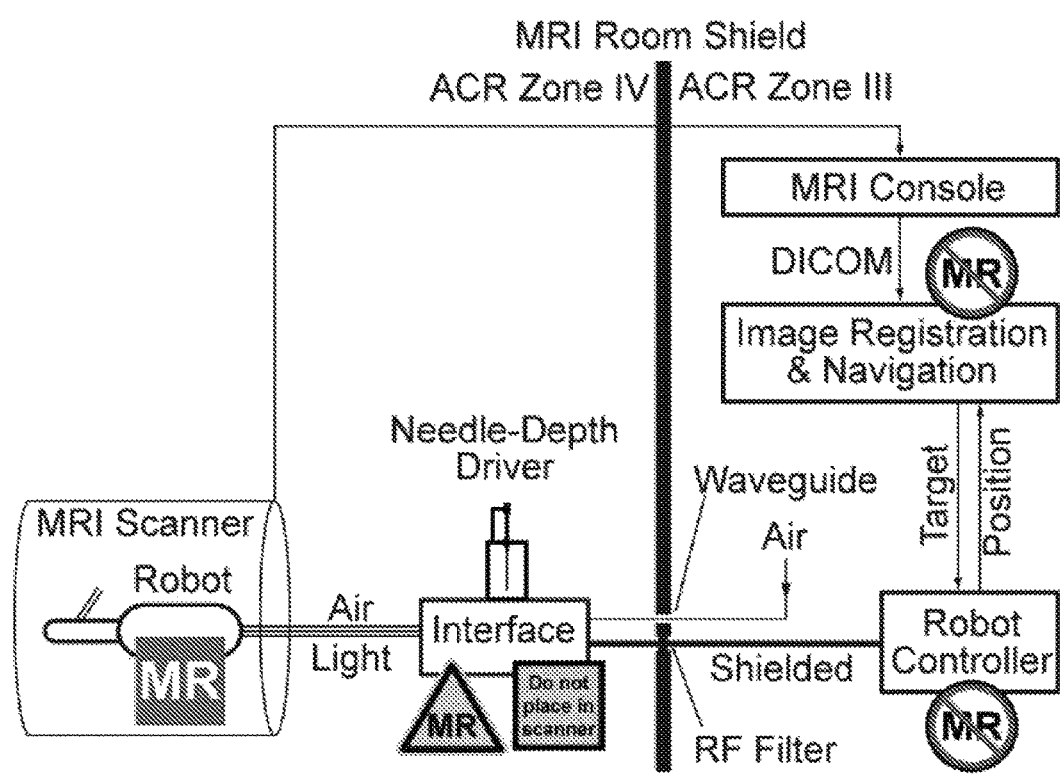
FIG. 9 illustrates a schematic of the robotic system according to the features of the present invention.

A schematic of the robotic system is presented in FIG. 9. This includes a new Interface controller that we developed for the biopsy robot. The Robot Controller is a PC based computer running Windows 7 (Microsoft Corp.) equipped with a motion control card (MCC)(MC4000, PMDI, Victoria, BC, Canada). This is MR-Unsafe and must remain outside the ACR Zone IV (scanner room), in the ACR Zone III (control room or MRI equipment room). The controller may take any other form suitable for controlling the robot and known to one of skill in the art, such as but not limited to a networked server, tablet, smartphone, microcontroller, or other non-windows based computing device.

As shown above, PneuStep motors use air pressure for actuation and light for the sensors. Electro-pneumatic and electro-optical interfaces are used to control the robot. The electro-pneumatic interface includes a PneuStep driver and a set of three pneumatic valves for each robot axis. The driver is a custom circuit that we developed for the PneuStep to convert the standard stepper pulse and direction signals from the MCC to pneumatic commutation signals. Standard voice-coil valves are magnetic. Being MRI-unsafe, these valves must be located in ACR Zone III. For the biopsy robot we updated the valves to a piezoelectric type (Hoerbiger/ Parker-Origa PS10021-641A). These use electricity but do not work magnetically. As such, the valves may be brought in the scanner room ACR Zone IV but outside the scanner. This reduces the length of the pneumatic hoses (3 m) improving the speed performance of the motors, and changes pneumatic and optical connectors to electrical, which are much simpler. The electro-optical interface is implemented with fiber optic sensors (D10 Expert, Banner Engineering Corporation). Overall the Interface box hosts the piezoelectric valves, drivers, and optical sensors. The Interface is nonmagnetic but includes metallic components and uses electricity. Therefore, the Interface is labeled MRI-conditional and it should not be placed within the scanner bore to avoid image artifacts.

Figure 10:
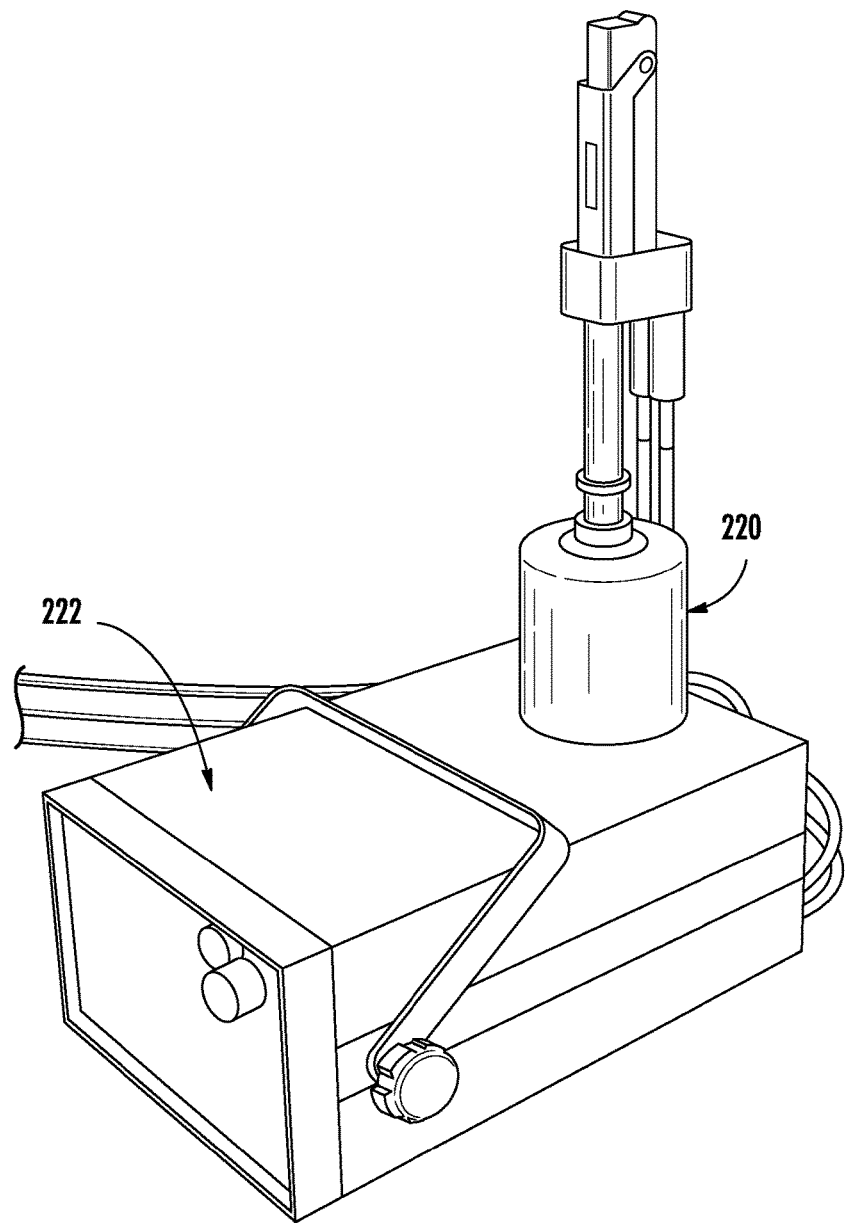
FIG. 10 illustrates a perspective view of an exemplary needle-depth driver mounted on the Interface box and representing the remote degree of freedom according to the features of the present invention.

The remote DoF device 220 that is used to preset the depth of needle insertion FIG. 7(*a*)-(*c*) is mounted on top of an Interface box 222, as shown in FIG. 10. Positioning the remote DoF device 220 next to the scanner is ergonomic for needle handling and allows for reduced hoses in the connections. This is an ergonomic location next to the scanner for needle handling and convenient for its connections avoiding additional hoses. Motion control, safety, and robot kinematics are implemented on the Robot controller PC under C++ (Visual Studio 2008, Microsoft Corp.) using libraries of the MCC. The Controller operates the robot in the robot space.

The present invention also includes safety features, such as a watchdog, emergency stop buttons, and visual alerts. This system design has been developed according to the Risk Hazard Analysis (RHA). The watchdog checks the state of several components of the system once every 100 ms, disabling power to the pneumatic valves of the electro-pneumatic interface, should a faulty condition occur. Since the system is pneumatically actuated, this disables the power of the motors.

The watchdog is built on hardware so that it is not influenced by software errors. In this approach software errors, which may be indeterministic, are mitigated by hardware design. The hardware watchdog monitors the activity of a software watchdog thread. In turn, the software watchdog may also disable power should a series of safety tests fail.

Visual signs are used to signal the operation state of the robot. Two Emergency Stop buttons may disable the system. One is located on the Robot Controller and the other on the Interface box next to the MRI.

Image-to-robot registration is used to register the MRI and the robot spaces, to control the robot in the image space. Images are acquired as usual and transferred over the network in DICOM format (Digital Imaging and Communications in Medicine) to the Image Registration & Navigation controller implemented on another PC.

Figure 11:
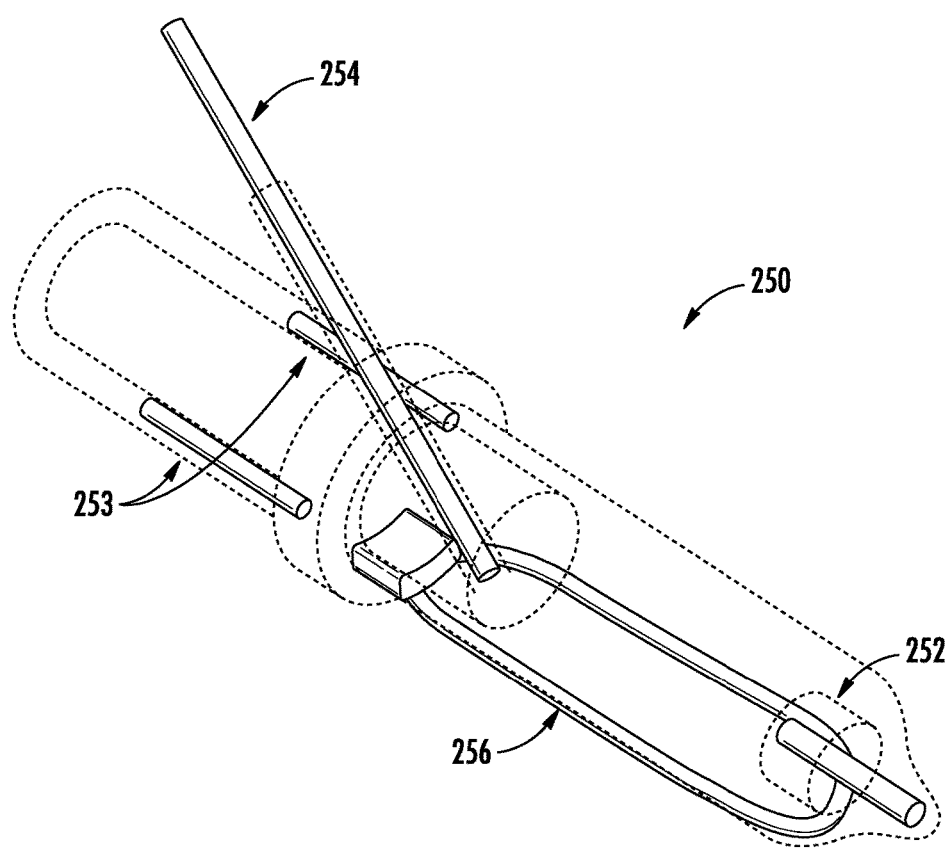
FIG. 11 illustrates a perspective view of the endorectal extension showing registration markers and built-in MRI coil according to the features of the present invention.

As illustrated in FIG. 11, the endorectal extension 250 includes a set of registration markers 252, 253, 254 and an MRI coil 256. The markers are plastic and glass tubes filled with MRI contrast (MR-Spots, Beekley Corporation, Bristol, Conn.). The MRI coil 256 is based on the MEDRAD BPX-30 (Warrendale, Pa.) coil.

The image-to-model registration method is used and implemented with custom modules in the Amira Visualization software (Visage Imaging, San Diego, Calif.). In this, a CAD model of the markers built in the robot coordinate system is superimposed over the MRI image of the markers. Then, the registration matrix is given by the relative position and orientation of the robot and image coordinate frames. This matrix enables the conversion of points between the two systems.

For example, when a target biopsy point is selected in the MRI, the registration converts it to robot coordinates. These are passed to the Robot controller, which through the inverse kinematics obtains the desired rotations (R1, R2) and depth setting (T) needed to aim the target. Conversely, if the robot is moved, the reversed transformations can simulate the location of the targeted biopsy point in the image space.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Bench Tests of Robot Precision and Accuracy: A set of experiments was conducted to determine the targeting performance of the robotic device independent of the imaging components. A 30×20×20 mm region within the workspace of the robot was divided in 10 mm interval, creating a target set of 36 target locations. A Polaris optical tracker (NDI, Canada) was used to measure the actual location of the needle point, with a passive marker mounted on the needle. A robot-to-Polaris space registration was performed using Arun's point-cloud method. A targeting error vector was defined as the difference between the corresponding points of the target and measured sets. The norm of the error vector ($\in = \sqrt{\in_x^2 + \in_y^2 + \in_z^2}$) was used to quantify targeting precision and accuracy using their standard definition, as the standard deviation respectively mean of the error norm data set.

Experimental results: show that the precision was 0.17 mm and the accuracy 0.37 mm.

Figure 12:
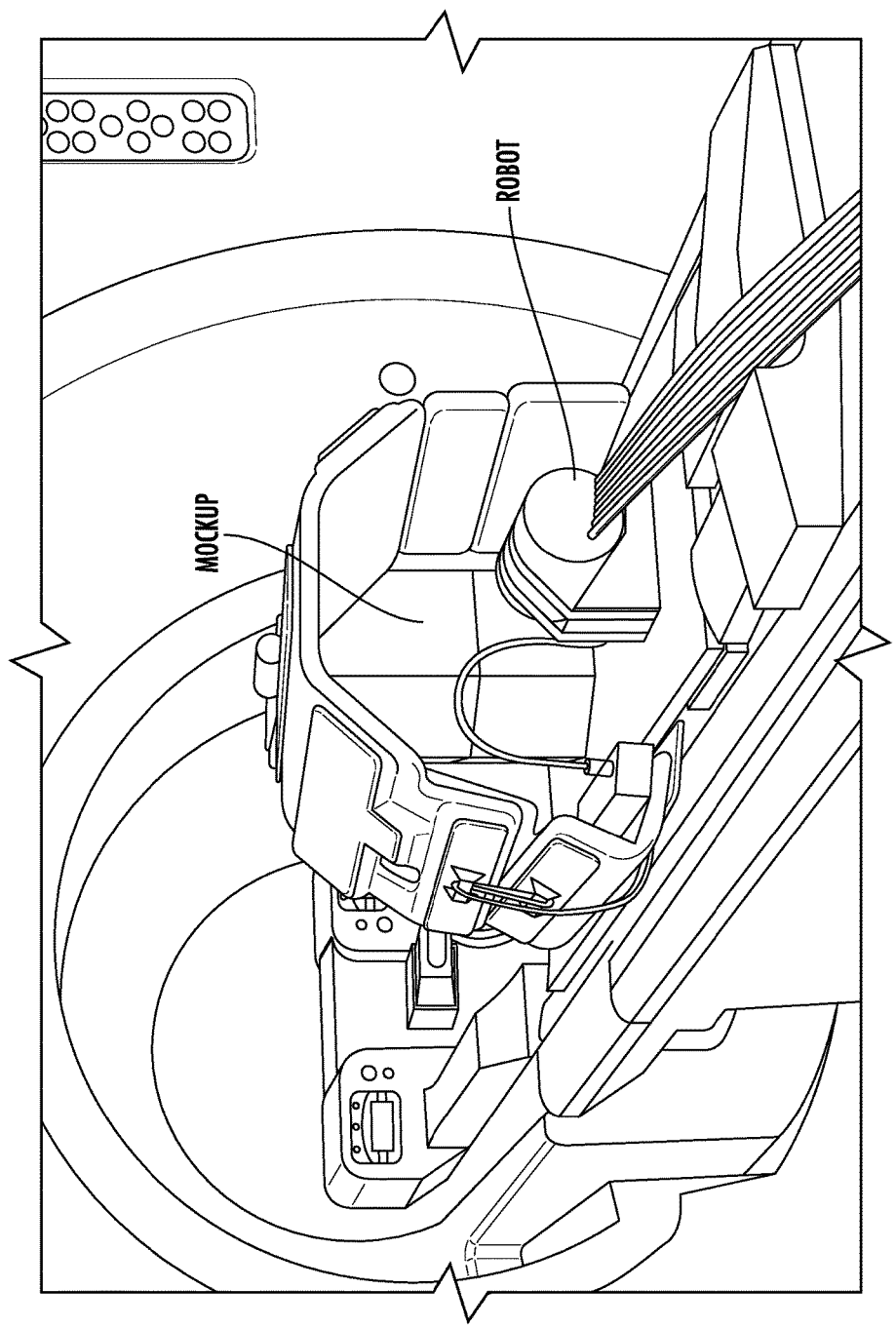
FIG. 12 illustrates a perspective view of a mockup used to simulate a "prostate" structure along with the robot device according to the features of the present invention.

MRI Tests: A mockup was built to simulate endorectal access to a "prostate" structure showing fine geometric patterns of lines and circles (Braino MRI test phantom). These were built in a gelatin base and placed in a plastic container (FIG. 12). Several tests were conducted to establish a quantitative image deterioration metric due to the presence of the instrument in the imaging field (EP—passive test) and by the activation and motion of the robotic instrument (EA—active test). The values of these measures ranges between 0% which corresponds to no deterioration and 100% which corresponds to total degradation of the images. Measures EP≤2% and EA≤1% are associated with minimal or unobservable image interference.

Two sets of the following experiments were performed on a 3-Tesla scanner to calculate the image deterioration factors as well as signal to noise ratio (SNR):
Sets NR: Reference image of the mockup without the robot.
Sets R: Image of the mockup with the robot in place, but not activated
Sets RM: Image of the mockup with the robot in motion All images were acquired with a pelvic phased-array coil, the built-in endorectal coil was not used for this experiment. This limitation was caused by the fact that the coil is part of the robot and, therefore, could not be used without the robot (NR Case).

Images of the geometric pattern (FIG. 13) show unperceivable differences between the NR, R, and RM sets. FIGS. 14(a) and (b) depict the passive (P) and active (A) coefficients as a function of the axial image slice from the phantom towards the robot, respectively. According to the methods presented in: Coefficient $\in^{P1}$ plots differences between two sets taken without the robot (NR1-NR2). Coefficient $\in^{P2}$ plots differences between two sets taken without and with the robot (NR1-R1). Coefficient $\in^{A1}$ plots differences between two sets taken with the robot (R1-R2). Coefficient $\in^{A2}$ plots differences between two sets taken with robot and with active robot (R1-RM1).

The area between the $\in^{P2}$ and $\in^{P1}$ plots in the region of the geometric mockup gives the passive image deterioration factor EP, and respectively the area between $\in^{A2}$ and $\in^{A1}$ plots gives the active factor EA.

The experimental values of the image deterioration factors are EP=0.117% and EA=0.004%. These values are below the 2% and 1% observable threshold, confirming that the presence and motion of the robot cause very slight, unobservable MRI changes.

Figure 14A:
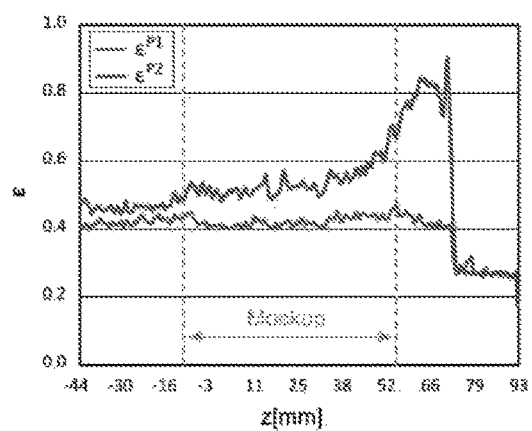
FIG. 14 (*a*) is a graphical representation of the passive (P) coefficients as a function of the axial image slice from the phantom toward the robot according to the features of the present invention.
Figure 14B:
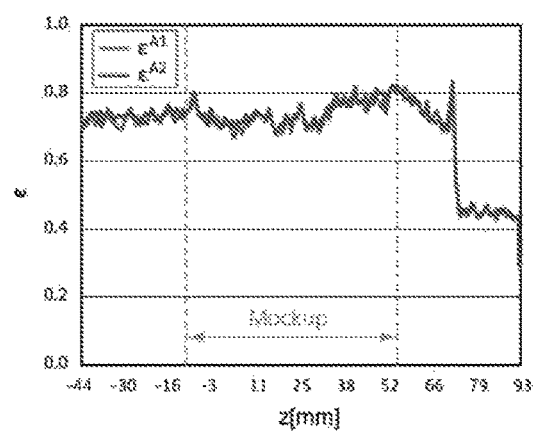
Figure 15:
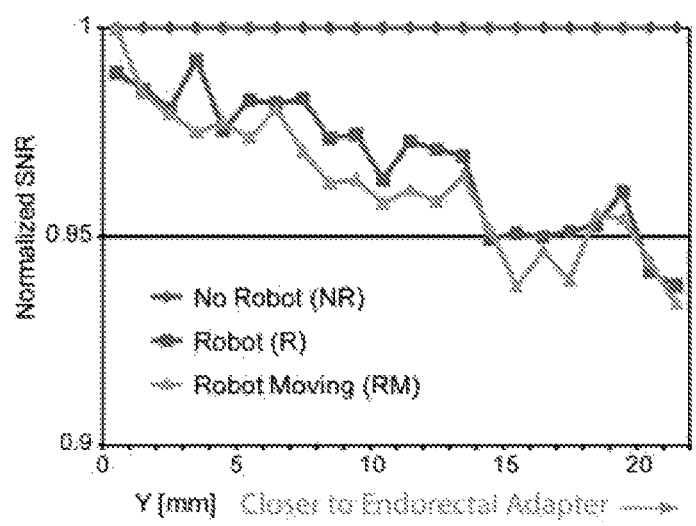
FIG. 15 is a graphical representation of SNR normalized to the NR case according to the features of the present invention.

Change in SNR due to the presence and motion of the robot in the imaging field have been calculated using the NEMA standard. The two image sets acquired for each case (NR1 & NR2, R1 & R2, RM1 & RM2) were used. Coronal (DICOM XZ plane) slices were used in this evaluation. For each slice the signal was calculated as the average pixel values over the entire slice. The noise was calculated as the standard deviation of the difference between the respective sets divided by square root of 2. Plots in FIGS. 14 (a) and (b) are normalized to the SNR of the no robot (NR) case (FIG. 15).

The graphs show a slight (5%) loss of signal in close proximity of the endorectal coil and minimal loss in the region of the prostate. We believe that the loss was caused by the disconnected coil. Unfortunately, we could not use the coil in this experiment because it is built in the robot that had to be removed for the NR case. Using another coil endorectal coil for the NR case would induce artificial differences, and removing the coil from the robot was impractical during the tests. The SNR plots also show that the additional loss of signal caused by the activation of the robot is minimal.

CT Tests: A robot that is MRI-safe is also compatible with other imaging equipment, multi-imager compatible, because the requirements imposed by the MRI are most stringent among all types. For example, typical image artifacts caused by metals in the CT are mitigated by the MRI-safe requirement of using nonmetallic materials. To demonstrate this, we have also performed in CT the MRI tests described above. Potentially, this expands the potential use of the robot-assistant device to other PCa imaging modalities such as PET-CT (Positron emission tomography). PET-CT has shown one of the most promising results to image advanced PCa. Similar to biopsy, the robot-assisted device could be extrapolated to guide therapy needles to the gland and para-prostatic locally advanced PCa tumors.

Figure 13:
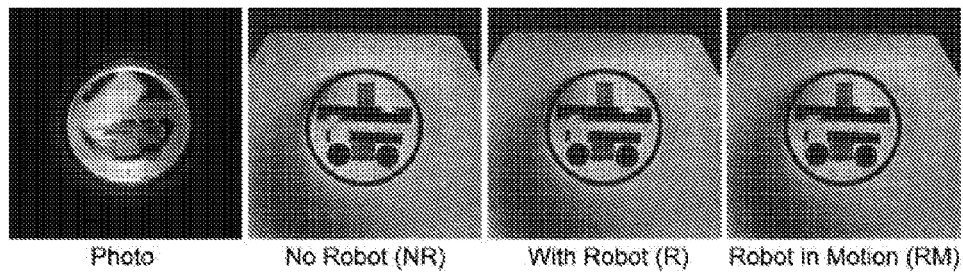
FIG. 13 illustrates MRI images of a fine geometric pattern mockup located in a gelatin base in place of the prostate according to the features of the present invention.
Figure 16:
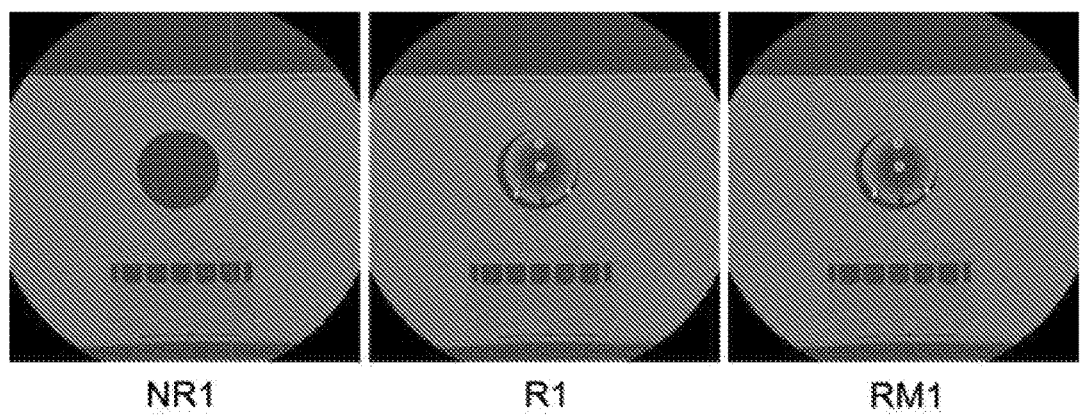
FIG. 16 illustrates a series of CT images of the fine geometric pattern mockup according to the features of the present invention.

The CT equivalent of FIG. 13 is FIG. 16, showing an example set of the no robot (NR), with the robot (R), and with robot motion (RM) axial image slices (DICOM XY plane) through the geometric mockup. The robot is visible in CT and ray-type artifacts from the MRI coil are observable. The corresponding image deterioration plots spike in the place of the visible features and artifacts. These show that preferably, the MRI coil will have to be removed if the robot is used for CT-guided interventions.

Ex-Vivo Biopsy Tissue Core Tests: A test was setup to assess possible differences between the tissue cores obtained with and without the use of the robot. One hundred cores were obtained in each case from the same ex-vivo animal tissue in a randomized order. Samples were collected with the same type 18Ga biopsy needles with 17 mm sample pocket opening length. The cores were analyzed blinded with respect to their acquisition method. Four measurements were taken for each core: (1) Number of core fragments; (2) the length of the longest fragment of the core [mm]; (3) the total length of the core [mm]; and (4) a qualitative score of the sample core: 1=Good, 2=Acceptable, 3=Poor.

Relative differences between the no robot and robot cases, for the four measurements above were very small: −4.49%, −2.40%, −1.26%, respectively 1.25%. If the biopsy needle is supported by the needle-guide the cores may be slightly longer.

In-vitro Image-Guided Needle Targeting Tests: Robot-assisted image-guided targeting tests have been performed with the MRI and CT. The measurement of the inserted needle location in the MRI is difficult due to typical artifacts at the needle point. To avoid it, we placed small cylindrical ceramic markers (seeds) through the trocar and retracted the needle. The implanted seed then marked the actual targeting point. The seeds were implanted as carefully as possible to reduce seed implantation (migration) errors.

A mockup was made with 16 O-rings (rubber, 5.0 mm inner diameter) embedded in a gelatin base. The center of each O-ring was targeted under MRI guidance and a seed was implanted. After implanting all seeds, the mockup was imaged with CT, for its higher accuracy. The targeting error vector was defined as the difference between the O-ring and seed centers, in a three dimensional (3-D) reconstruction of the CT images. The norm of the error vector was used to quantify targeting precision and accuracy as the standard deviation respectively mean of the error norm data set.

Experimental results show that the precision was 1.32 mm and the accuracy 2.09 mm. These include unquantified seed implantation errors. However, this was the most accurate measurement method that we could find for the MRI-guided test.

For the CT-guided experiment, however, we could exclude seed implantation errors because the needle-point may be directly imaged in CT. A gelatin mockup was imaged together with the robot, and the registration was performed. Then, 24 target points were selected in the CT image space, were successively targeted with the needle point, and CT images at the needle point were acquired after each insertion to measure the actual locations. A targeting error vector was defined as the difference between the target and actual point of the inserted needle in the image space. The norm of the error vector was used to quantify targeting precision and accuracy, as the standard deviation respectively mean of the error norm data set.

Experimental results show that the precision was 0.33 mm and the accuracy 1.10 mm. Animal Study: A survival animal study on 6 male Beagle dogs was performed at the MSKCC with approval of the Institutional Animal Care and Use Committee (IACUC) and clearance of the DoD Animal Care and Use Review Office (ACURO).

Figures 17A, 17B:
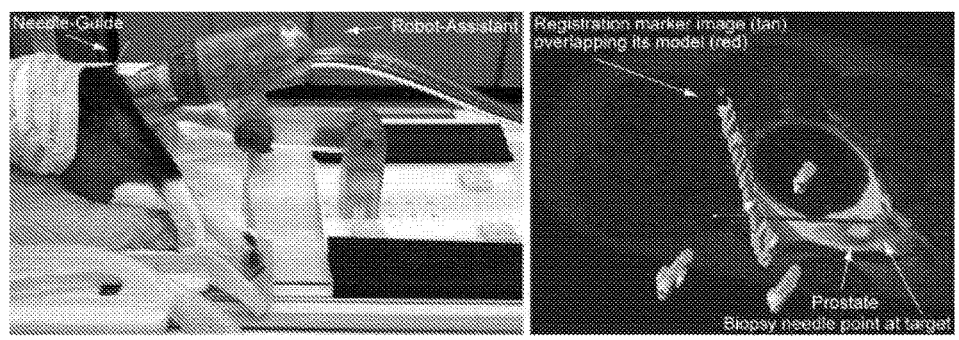
FIG. 17(*a*) illustrates a perspective view of an MRI-guided biopsy animal experiment according to the features of the present invention.

Under general anesthesia, the dogs were placed prone on the MRI table on support pads (FIG. 17(a)). The endorectal extension of the robot was placed transrectally and the robot locked in place. The built-in endorectal and a pelvic phased-array coil were used concurrently. Images of the marker were used for registration. Images of the prostate were used to select targets. Due to the small size of the prostate in dogs 4-6 targets were selects for each dog. These were targeted with the needle and MRI was acquired to measure the actual locations. FIG. 17(b) shows an example of the image navigation screen showing the superimposed registration markers (tan-image over red-model), the prostate and the inserted needle model. Targeting error vectors were calculated as the difference between the target and actual locations in the image space. The norm of the error vector was used to quantify targeting precision and accuracy, as the standard deviation respectively mean of the error norm data set.

Figure 18:
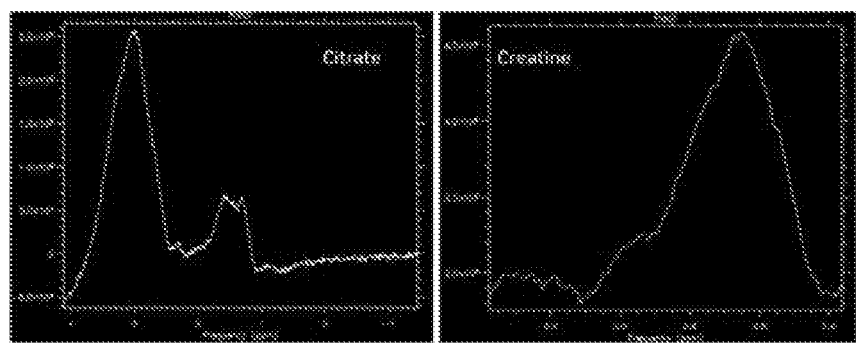
FIG. 18 illustrates graphical representations of animal experiment MRSI voxel data according to the features of the present invention.

Experimental results over the 6-dog dataset show a targeting precision of 1.31 mm and accuracy of 2.58 mm. Actual values are likely smaller because these values include measurement errors caused by the needle artifact. In the animal studies, we have also conducted experiments to observe if the robot may deteriorate MR spectroscopy images (MRSI), as in the following clinical studies spectroscopy may be used to highlight CSR for biopsy targeting. The study was performed on 3 dogs. A single voxel was selected within the prostate due to the small size of the prostate and the scope of the test. A sample from one of the dogs processed with the Prostate Spectroscopy and Imaging Exam software (Prose, GE Healthcare, Waukesha, Wis.) is presented in FIG. 18. As these dogs were healthy, there was no Choline peak to analyze. But the MRSI indicated no changes in the peak or location of the Citrate and Creatine peaks before or after robot placement. After the experiments all 6 dogs recovered and have been adopted.

In summary, the present invention is a novel robotic assisted device for MRI-guided prostate biopsy. This uses a pneumatic actuation technology, which is uniquely capable to drive an MRI-safe and precise robotic device. The device is exclusively made of non-metallic components and is electricity free. The robot was tested preclinically. In short, the robot is safe to use in any MRI environment (MRI-safe), is not influenced by the MRI and does not interfere with the functionality of the MRI, the quality of the biopsy cores is not worse than manually collected, and needle targeting precision and accuracy are very good. Table 1 summarizes the precision and accuracy results.

TABLE 1

Summary of robot precision and accuracy

| | Precision [mm] | Accuracy [mm] | Measurement Limitations |
|---|---|---|---|
| Bench tests | 0.17 | 0.37 | — |
| CT-guided, in vitro | 0.33 | 1.10 | — |
| MRI-guided, in vitro | 1.32 | 2.09 | Include seed implant errors |
| MRI-guided, animal | 1.31 | 2.58 | Include MRI artifact errors |

MRI-guided experiments include inherent measurement errors, thus actual results may be superior. The size of a clinically significant PCa tumor is 0.5 mL, corresponding to a spherical shape of approximately 5 mm radius. Because in all experiments targeting accuracy was smaller than 5 mm, these results suggest that the device is sufficiently accurate to guide needle placement for prostate biopsy.

The device has a significant potential. Clinically, targeted biopsies have the potential to sample more significant lesions in lieu of the currently overdetected insignificant cancers. If validated for biopsy, the device and methods could then be extrapolated to focal therapy delivery. The device is primarily guided by MRI, but the device is multi-imager compatible. In the long-term, the device could be guided by PET-CT, which has shown great potential to image advanced PCa, to deliver focal therapy to help patients with recurrent PCa after radical prostatectomy or radiation therapy.

The device also presents a significant potential as a research tool. An image-guide biopsy targeting could provide a valuable instrument to correlate PCa imaging with pathology. Devices to provide accurate biopsy samples are currently unavailable and PCa remains the only cancer that still requires further validation. The device may also be a valuable instrument for the development of PCa biomarkers and chemopreventive agents, as it could provide repeat biopsies of the same site to monitor the progression of the disease over time and the response to chemopreventive agents. Such instruments are currently unavailable.

Targeted biopsies may also have a significant economic impact, as these may reduce the healthcare burden that is currently associated with the treatment and management of PCa. First, targeted biopsies may reduce the overdiagnosis of PCa that is related to its overtreatment. A larger part of the estimated 241,740 PCa diagnosed each year in the US alone could then be directed towards less aggressive and less expensive treatment options such as cryotherapy and active surveillance programs. This paradigm change may reduce our burden of nearly $2 billion estimated to be spent on radical prostatectomy and radiation therapy. Second, reliable targeted biopsies have the potential to reduce the number of repeat biopsies which now approach $1 billion yearly.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. An MRI safe robot for guiding transrectal prostate biopsy, comprising:
a support arm;
a robot body operatively connected to said support arm;
a transrectal biopsy device operatively connected to said robot body, said transrectal biopsy device including an endorectal extension and a biopsy needle device, said endorectal extension including an MRI coil for creating MRI images of a prostate; and
said robot body including a first driver module for generating rotational motion of said endorectal extension and a second driver module for angulating said biopsy needle device toward a target area of the prostate for biopsy, said biopsy needle device being rotatable relative to the endorectal extension about a fixed axis and translatable through said endorectal extension, each of said first and second driver modules including at least one pneumatic motor;
wherein said MRI images are used by a physician to determine the target area of the prostate for biopsy.

2. The robot of claim 1, further including a robot controller for automatically orienting the transrectal biopsy device to the target area of the prostate for biopsy as selected by the physician.

3. The robot of claim 1, wherein the endorectal extension includes a set of registration markers for image-to-robot registration.

4. The robot of claim 1, wherein the biopsy needle device includes a needle guide and needle spacer, said needle guide passing through said endorectal extension and having a revolute joint for keeping the needle guide as close as possible to the target area of the prostate independent of its angulation.

5. The robot of claim 1, wherein said first driver module and said second driver module are coaxially arranged.

6. The robot of claim 5, wherein said second driver module drives an output shaft that passes through said first driver module and engages a screw of the transmission actuating angulation of said biopsy needle device.

7. The robot of claim 1, wherein said first driver module includes an output shaft that engages a wave generator of a harmonic transmission.

8. The robot of claim 6, wherein said harmonic transmission is coaxially arranged with said first and second drive modules.

9. The robot of claim 1, further comprising a remote robotic device for automatically presetting a depth of needle insertion.

10. The robot of claim 9, wherein the remote robotic device is powered by a third pneumatic motor.

11. A robot-assisted method for biopsy of a prostate, comprising:
provinding a robot including a transrectal biopsy device having an endorectal extension powered by a first pneumatic motor and a biopsy needle device powered by a second pneumatic motor, said endorectal extension including an MRI coil for MRI imaging of the prostate;
imaging a region of interest by MRI imaging to create MRI images;
displaying the MRI images;
selecting a target area of interest based upon the MRI images; and
directing the robot to automatically orient the transrectal biopsy device towards the target area selected by rotating the endorectal extension and angulating the biopsy needle device.

12. The method of claim 11, further comprising:
providing a remote robotic device for automatically presetting a depth of needle insertion.

13. The method of claim 12, wherein a needle spacer is automatically adjusted by the remote robotic device upon selection of the target area, said needle spacer for setting the needle depth.

14. The method of claim 11, further including passing a needle guide through the endorectal extension at an angle, wherein the angle is automatically adjusted by the robot upon selection of the target area.

\* \* \* \* \*